United States Patent
Palushi et al.

(10) Patent No.: US 11,273,293 B2
(45) Date of Patent: Mar. 15, 2022

(54) SINUPLASTY INSTRUMENT WITH DEFLECTABLE GUIDE RAIL

(71) Applicant: Acclarent, Inc., Irvine, CA (US)

(72) Inventors: Jetmir Palushi, Irvine, CA (US); Athanasios Papadakis, Newport Beach, CA (US); Itzhak Fang, Irvine, CA (US); Jordan R. Trott, Redondo Beach, CA (US)

(73) Assignee: Acclarent, Inc., Irvine, CA (US)

( * ) Notice: Subject to any disclaimer, the term of this patent is extended or adjusted under 35 U.S.C. 154(b) by 158 days.

(21) Appl. No.: 16/665,128

(22) Filed: Oct. 28, 2019

(65) Prior Publication Data
US 2020/0197670 A1    Jun. 25, 2020

Related U.S. Application Data

(60) Provisional application No. 62/783,252, filed on Dec. 21, 2018.

(51) Int. Cl.
| | |
|---|---|
| *A61M 25/10* | (2013.01) |
| *A61M 25/06* | (2006.01) |
| *A61M 25/00* | (2006.01) |
| A61B 1/233 | (2006.01) |
| A61B 1/06 | (2006.01) |
| A61M 25/09 | (2006.01) |

(52) U.S. Cl.
CPC ........ *A61M 25/10* (2013.01); *A61M 25/0023* (2013.01); *A61M 25/0662* (2013.01); *A61B 1/06* (2013.01); *A61B 1/233* (2013.01); *A61M 25/0054* (2013.01); *A61M 2025/0024* (2013.01); *A61M 2025/0687* (2013.01); *A61M 2025/09008* (2013.01)

(58) Field of Classification Search
CPC .......... A61B 1/233; A61M 2025/0024; A61M 2025/09008; A61M 25/0054; A61M 25/0662; A61M 25/10
See application file for complete search history.

(56) References Cited

U.S. PATENT DOCUMENTS

| | | | |
|---|---|---|---|
| 9,155,492 | B2 | 10/2015 | Jenkins et al. |
| 10,137,286 | B2 | 11/2018 | Lin et al. |
| 2010/0274188 | A1 | 10/2010 | Chang et al. |
| 2011/0004057 | A1 | 1/2011 | Goldfarb et al. |
| 2013/0274715 | A1 | 10/2013 | Chan et al. |
| 2016/0008083 | A1 | 1/2016 | Kesten et al. |
| 2018/0214216 | A1 | 8/2018 | Sema et al. |
| 2018/0311472 | A1 | 11/2018 | Matlock et al. |
| 2019/0015646 | A1 | 1/2019 | Matlock et al. |
| 2019/0192177 | A1 | 6/2019 | Palushi et al. |

*Primary Examiner* — Deanna K Hall
(74) *Attorney, Agent, or Firm* — Frost Brown Todd LLC

(57) ABSTRACT

An apparatus includes a body, a first shaft, an actuation assembly, and a dilation catheter. The first shaft includes a malleable distal portion. The actuation assembly includes a second shaft and an actuator. The second shaft is coaxially positioned about the first shaft. The actuator is operable to selectively bend the malleable distal portion of the first shaft. The dilation catheter is coaxially interposed between the first shaft and the second shaft. The dilation catheter includes an expandable dilator. The dilation catheter is operable to translate along the malleable distal portion of the first shaft.

18 Claims, 15 Drawing Sheets

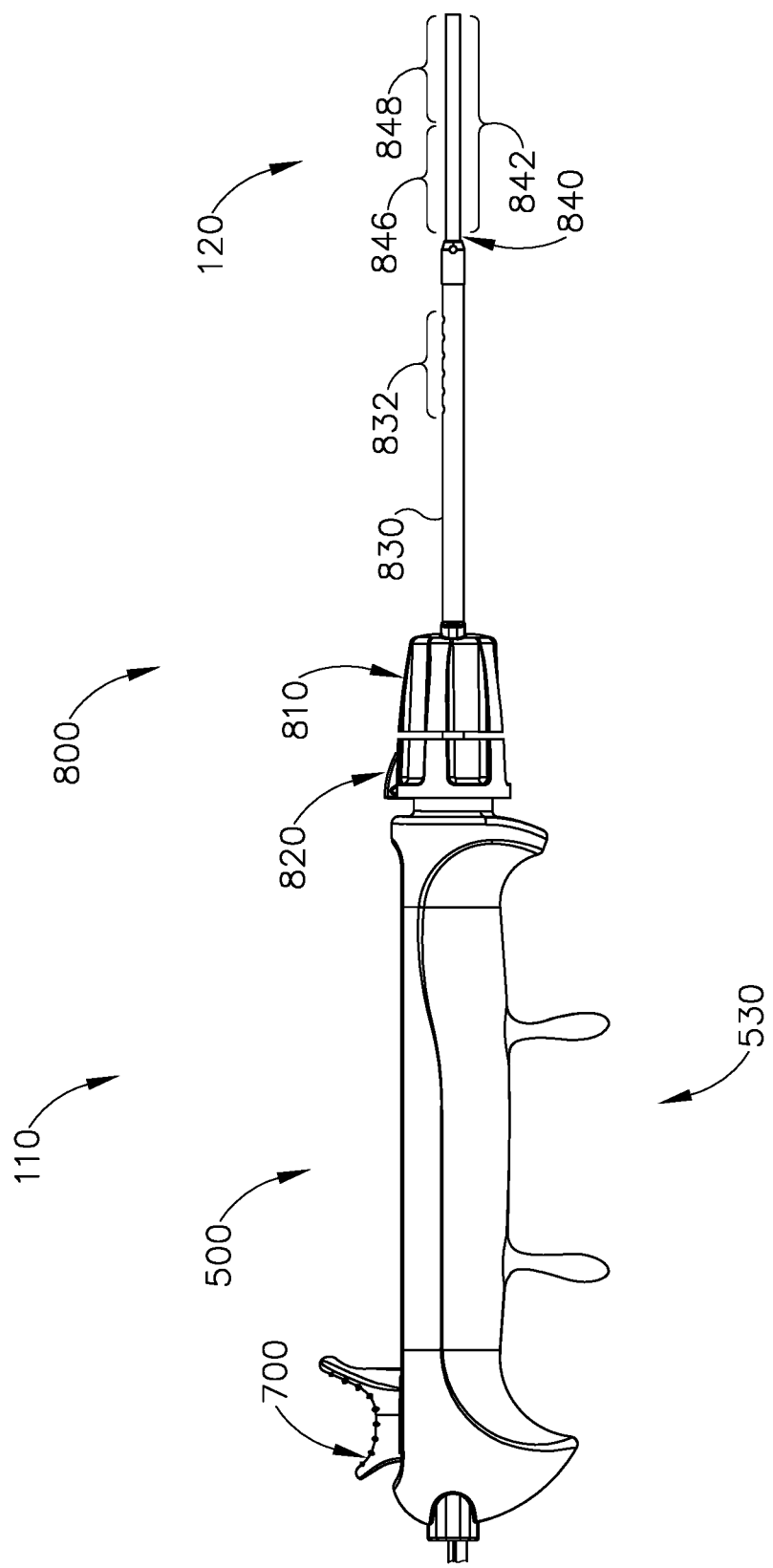

SINUPLASTY INSTRUMENT WITH DEFLECTABLE GUIDE RAIL

PRIORITY

This application claims priority to U.S. Provisional Pat. App. No. 62/783,252, entitled "Sinuplasty Instrument with Deflectable Guide Rail," filed Dec. 21, 2018, the disclosure of which is incorporated by reference herein.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guidewire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Relieva® Spin Balloon Sinuplasty™ System by Acclarent, Inc. of Irvine, Calif.

In the context of Eustachian tube dilation, a dilation catheter or other dilation instrument may be inserted into the Eustachian tube and then be inflated or otherwise expanded to thereby dilate the Eustachian tube. The dilated Eustachian tube may provide improved ventilation from the nasopharynx to the middle ear and further provide improved drainage from the middle ear to the nasopharynx. Methods and devices for dilating the Eustachian tube are disclosed in U.S. Patent Pub. No. 2010/0274188, entitled "Method and System for Treating Target Tissue within the ET," published on Oct. 28, 2010, now abandoned, the disclosure of which is incorporated by reference herein; and U.S. Patent Pub. No. 2013/0274715, entitled "Method and System for Eustachian Tube Dilation," published on Oct. 17, 2013, now abandoned, the disclosure of which is incorporated by reference herein. An example of such a system is the Aera® Eustachian Tube Balloon Dilation System by Acclarent, Inc. of Irvine, Calif.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue (e.g., hypodermis, subdermis, etc.) and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pat. No. 9,155,492, entitled "Sinus Illumination Lightwire Device," issued Oct. 13, 2015, the disclosure of which is incorporated by reference herein. An example of such an illuminating guidewire is the Relieva Luma Sentry® Sinus Illumination System by Acclarent, Inc. of Irvine, Calif.

Balloon sinuplasty procedures may be performed using a dilation catheter that is either slidably coupled with a guide catheter (e.g., such that the dilation catheter is positioned in the guide catheter); or with a guide rail (e.g., such that the dilation catheter is positioned about the exterior of the guide rail). In either case, it may be beneficial to bend the guide to achieve a particular bend angle that will facilitate insertion of the dilation catheter in a particular anatomical passageway in the head of the patient. For instance, it may be beneficial for the guide to provide a substantially straight configuration to guide the dilation catheter into a sphenoid sinus ostium; a bend angle of approximately 55 degrees to guide the dilation catheter into a Eustachian tube; a bend angle of approximately 70 degrees to guide the dilation catheter into a frontal recess; or a bend angle of approximately 110 degrees to guide the dilation catheter into a maxillary sinus ostium.

It may be desirable to facilitate bending of a guide in order to achieve various bend angles, thereby facilitating guidance of a dilation catheter into various different anatomical passageways in the head of a patient, including in procedures that will be performed only by a single operator. While several systems and methods have been made and used to position a balloon of a dilation catheter in an anatomical passageway, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 5A depicts a side view of the dilation instrument of FIG. 4, with a deflection actuation assembly in a proximal position, and with a guide shaft in a straight configuration;

Figure 1A:
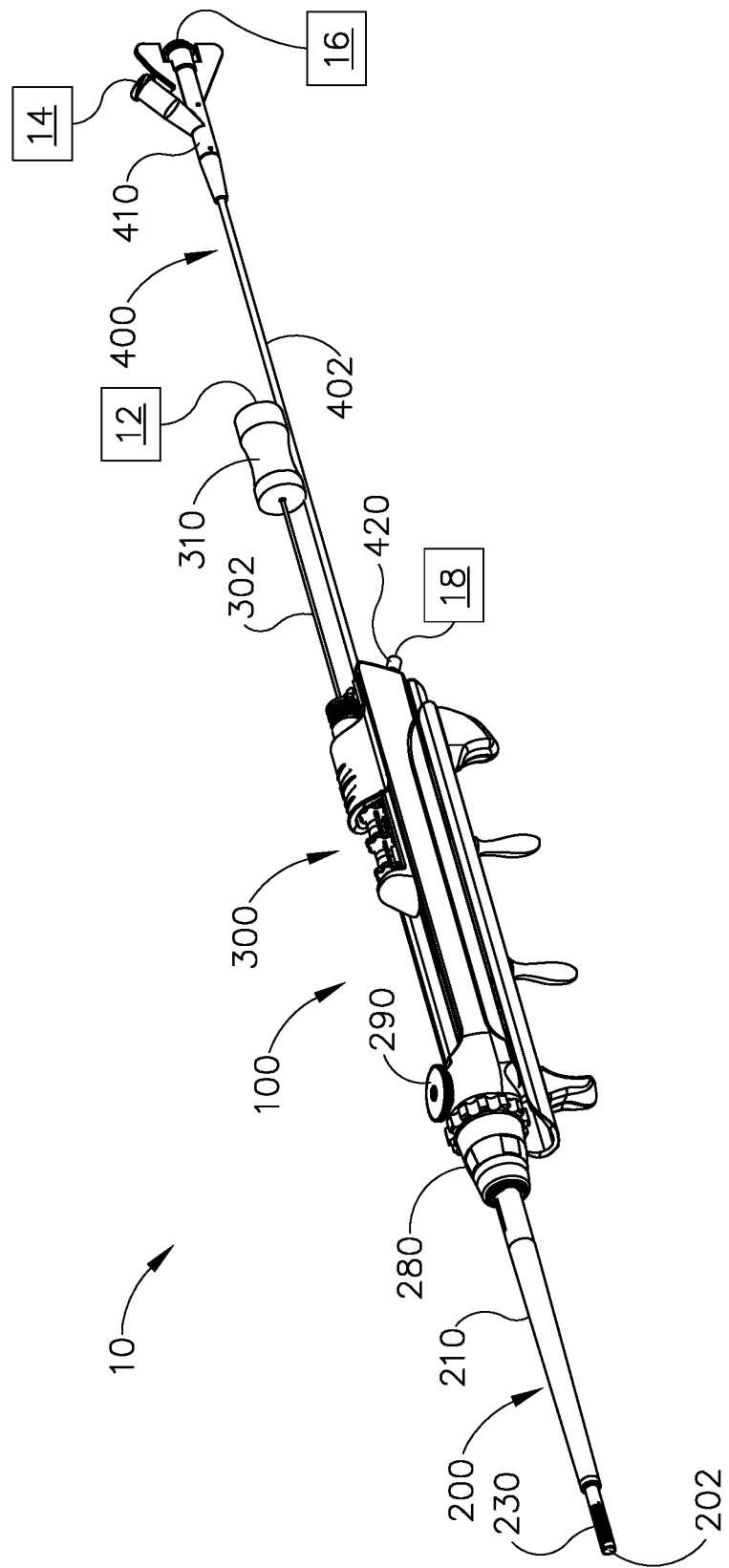
FIG. 1A depicts a perspective view of an exemplary dilation instrument, with a guidewire and a dilation catheter each in respective proximal positions.
Figure 1B:
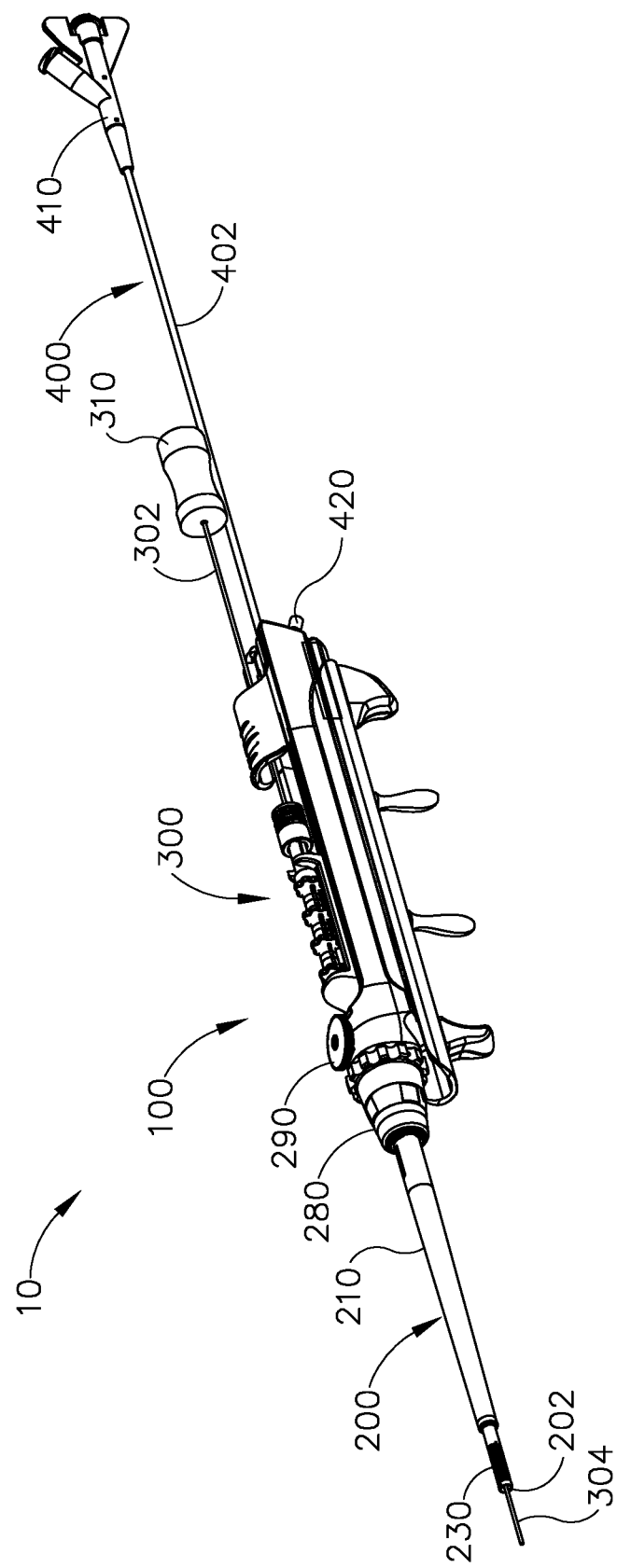
FIG. 1B depicts a perspective view of the instrument of FIG. 1A, with the guidewire in a distal position and the dilation catheter in the proximal position.
Figure 1C:
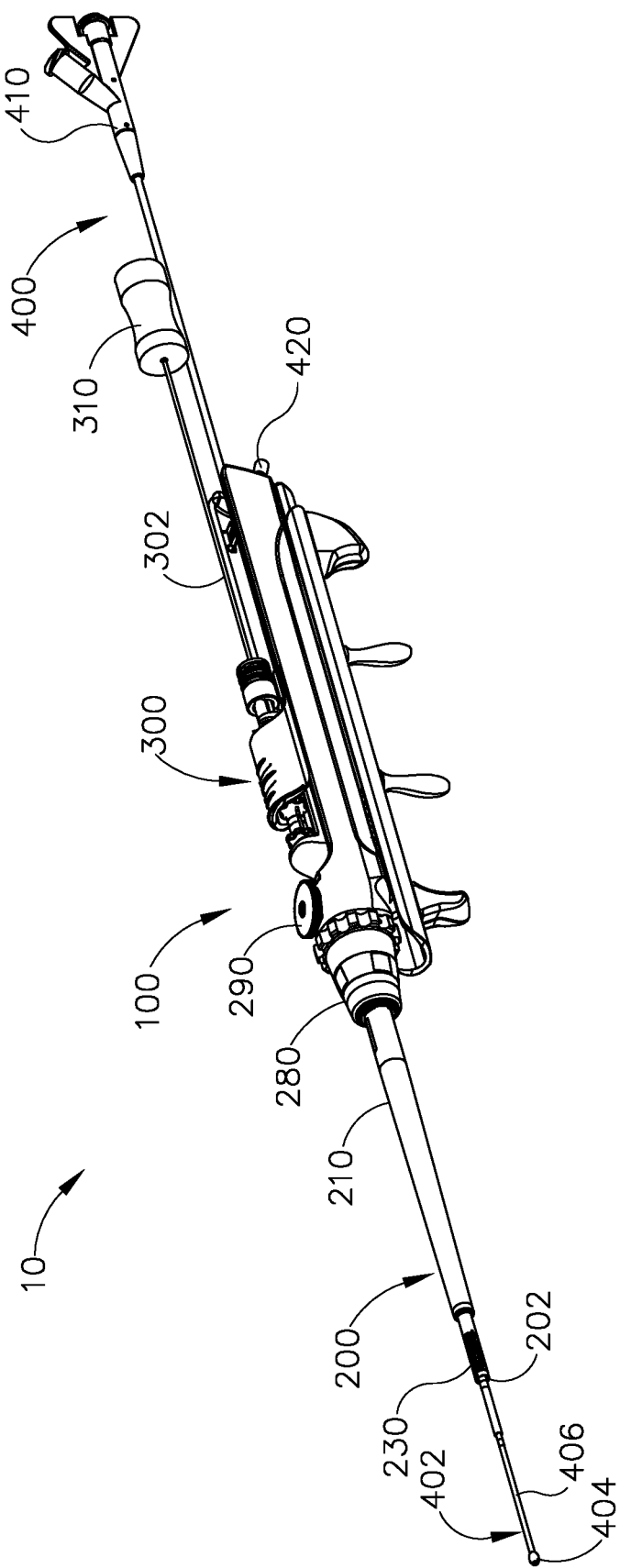
FIG. 1C depicts a perspective view of the instrument of FIG. 1A, with the guidewire and the dilation catheter each in respective distal positions, and with a dilator of the dilation catheter in a non-expanded state.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. For example, while various. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Dilation Instrument with External Deflectable Guide Shaft

FIGS. 1A-1D show an exemplary dilation instrument (10) that may be used to dilate an ostium or other passageway associated with drainage of a paranasal sinus, a Eustachian tube, or some other anatomical passageway (e.g., within the ear, nose, or throat, etc.). As will be described in greater detail below, dilation instrument (10) of the present example provides adjustability that enables the operator to use dilation instrument (10) in different scenarios, without requiring the operator to switch between different instruments. For instance, dilation instrument (10) may be used to dilate various different anatomical passageways (e.g., frontal sinus ostium, frontal recess, maxillary sinus ostium, sphenoid sinus ostium, ethmoid sinus ostium, Eustachian tube, etc.) by making simple adjustments to structural features of the instrument.

Dilation instrument (10) of this example includes a handle assembly (100), a guide shaft assembly (200) extending distally from handle assembly (100); a guidewire actuation assembly (300) slidably coupled with handle assembly (100); and a dilation catheter actuation assembly (400) slidably coupled with handle assembly (100). A guidewire module (12) is coupled with a guidewire (302) of instrument (10) via a connector (310). An inflation fluid source (14) and an irrigation fluid source (16) are fluidly coupled with a dilation catheter (402) of instrument (10) via a connector (410). A suction source (18) is coupled with a suction port (420) of instrument (100).

Figure 1D:
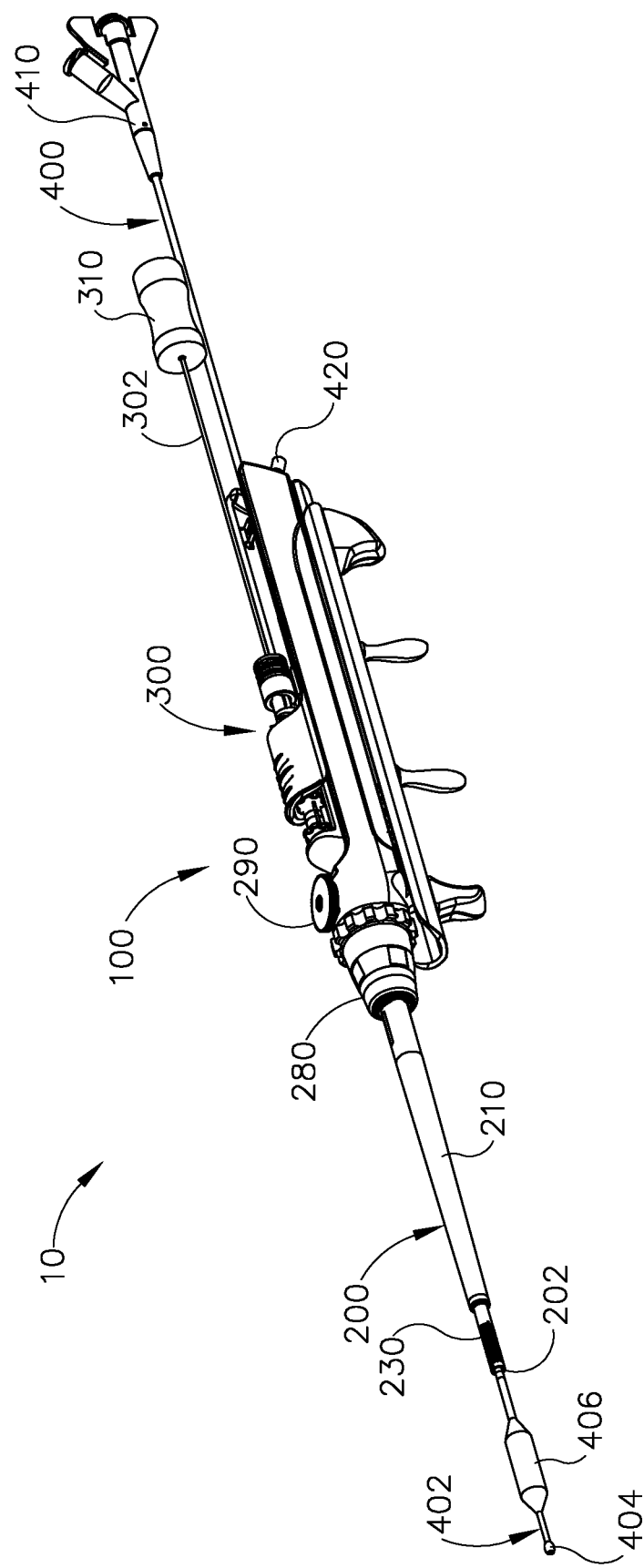
FIG. 1D depicts a perspective view of the instrument of FIG. 1A, with the guidewire and the dilation catheter each in respective distal positions, and with a dilator of the dilation catheter in an expanded state.

Handle assembly (100) is sized and configured to be grasped and operated by a single hand of an operator. The operator may selectively operate guidewire actuation assembly (300) and dilation catheter actuation assembly (400) with the same single hand that grasps handle assembly (100). As shown in the transition from FIG. 1A to FIG. 1B, the operator may advance guidewire actuation assembly (300) distally along handle assembly (100) to thereby advance guidewire (302) distally, such that a distal end (304) of guidewire (302) is positioned distal to the distal end of guide shaft assembly (200). As shown in the transition from FIG. 1B to FIG. 1C, the operator may then advance dilation catheter actuation assembly (400) distally along handle assembly (100) to thereby advance a dilation catheter (402) distally along guidewire (302), such that the distal tip (404) of dilation catheter (402) is positioned distal to the distal end of guide shaft assembly (200). With dilation catheter (402) advanced to a distal position, the operator may then inflate a dilator (406) of dilation catheter (402) to achieve an expanded state as shown in FIG. 1D, to thereby dilate an anatomical passageway in which dilator (406) is positioned. In the present example, dilation catheter (402) is coaxially disposed within guide shaft assembly (200), and guidewire (302) is coaxially disposed within dilation catheter (402). In other examples, guide shaft assembly (200) may be coaxially disposed within dilation catheter (402), and guidewire (302) may be coaxially disposed within guide shaft assembly (200).

In some versions of dilation instrument (10), guidewire (302) may include one or more optical fibers, and distal end (304) may be configured to emit visible light. In some such versions, guidewire module (12) includes a light source, and connector (310) is operable to communicate light from the light source of guidewire module (12) to guidewire (302). Illuminating versions of guidewire (302) may be used to provide position confirmation through observation of transillumination effects. By way of example only, illuminating versions of guidewire (302) may be constructed and operable in accordance with at least some of the teachings of U.S. Pat. No. 9,155,492, entitled "Sinus Illumination Lightwire Device," issued Oct. 13, 2015, the disclosure of which is incorporated by reference herein.

In addition to providing illumination, or as an alternative to providing illumination, guidewire (302) may provide position sensing capabilities. In some such versions, the distal end of guidewire (302) may include a position sensor. By way of example only, such a guidewire (302) may be constructed and operable in accordance with at least some of the teachings of U.S. Pub. No. 2018/0214216, entitled "Navigation Guidewire with Interlocked Coils," published Aug. 2, 2018, issued as U.S. Pat. No. 10,610,308 on Apr. 7, 2020; U.S. Pub. No. 2019/0192177, entitled "Reusable Navigation Guidewire," published Jun. 27, 2019; and/or U.S. Pub. No. 2016/0008083, entitled "Guidewire Navigation for Sinuplasty," published Jan. 14, 2016, issued as U.S. Pat. No. 10,463,242 on Nov. 5, 2019, the disclosures of each of these references being incorporated by reference herein. In some such versions, guidewire module (12) includes an image-guided surgery (IGS) navigation system, and connector (310) is operable to communicate position-indicative signals from the position sensor of guidewire (302) to guidewire module (12). In other versions of dilation instrument (10), guidewire (302) may be omitted entirely.

A. Exemplary Guide Shaft Assembly and Associated Actuation Assemblies

Figure 2:
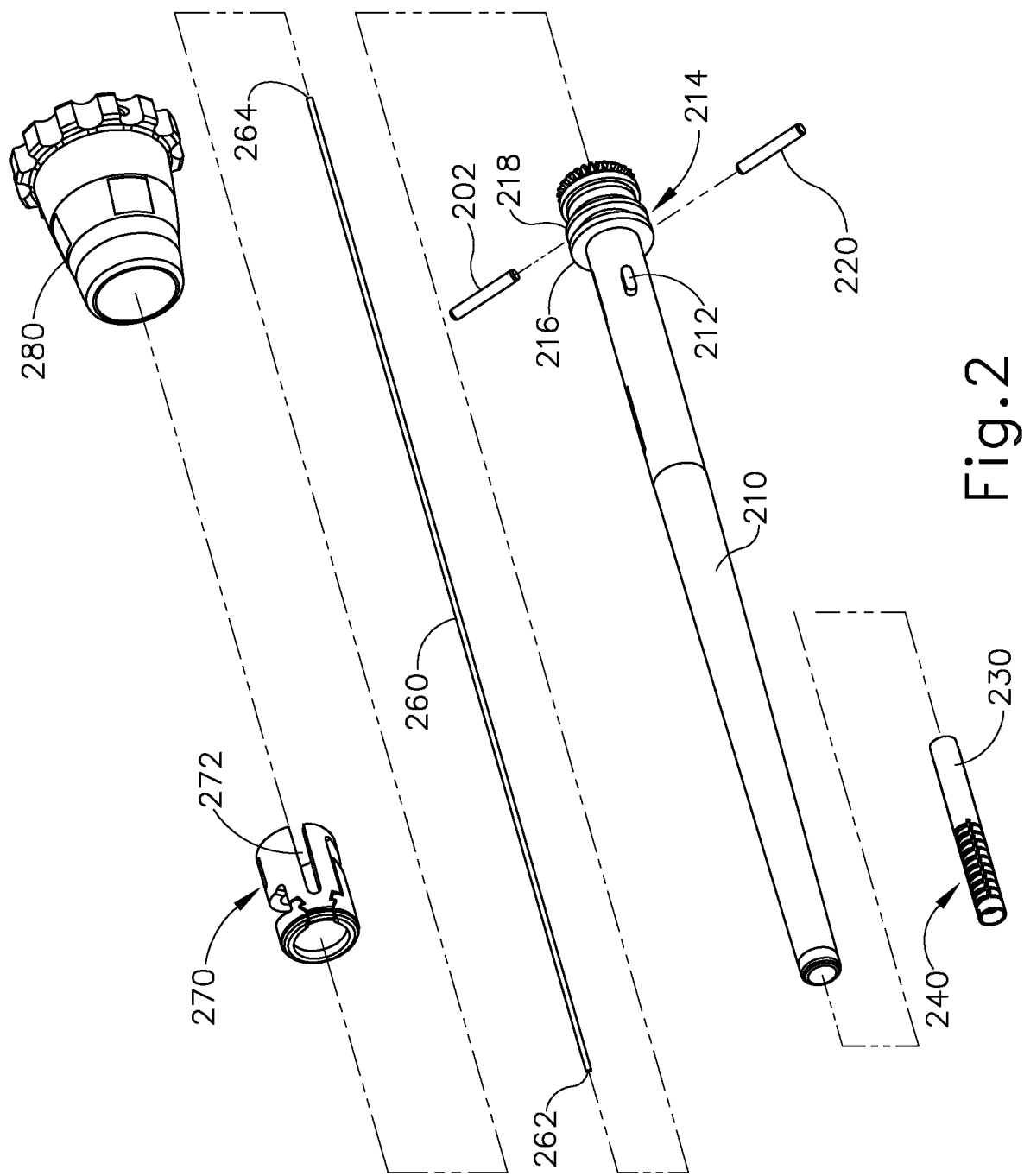
FIG. 2 depicts an exploded perspective view of a guide shaft assembly of the instrument of FIG. 1A.

As shown in FIGS. 2-3, guide shaft assembly (200) of the present example includes a rigid shaft member (210), a flexible shaft member (230) arranged at the distal end of rigid shaft member (210), a push-pull wire (260), a cam barrel (270), and a deflection control knob (280). Shaft members (210, 230), cam barrel (270), and deflection control knob (280) are coaxially aligned with each other in this example, with push-pull wire (260) being laterally offset from the central longitudinal axis shared by shaft members (210, 230), cam barrel (270), and deflection control knob (280). Shaft assembly (200) is operable to guide guidewire (302) and dilation catheter (402) along an operator-selected exit angle relative to the central longitudinal axis of guide shaft assembly (200).

Figure 3A:
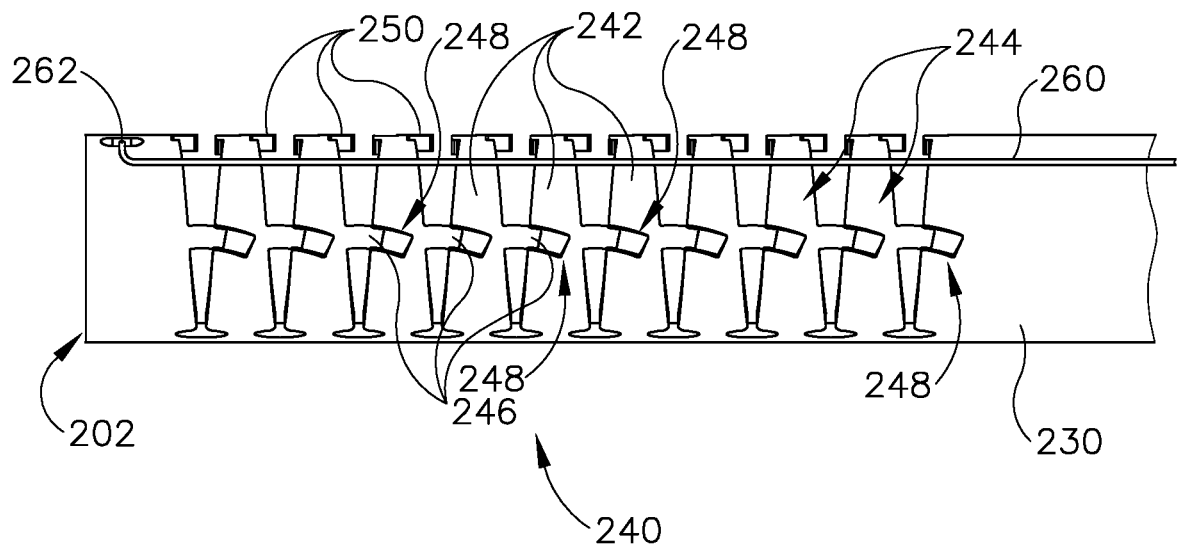
FIG. 3A depicts a cross-sectional side view of a distal portion of a flexible shaft member of the guide shaft assembly of FIG. 2, with the distal portion in a straight configuration.
Figure 3B:
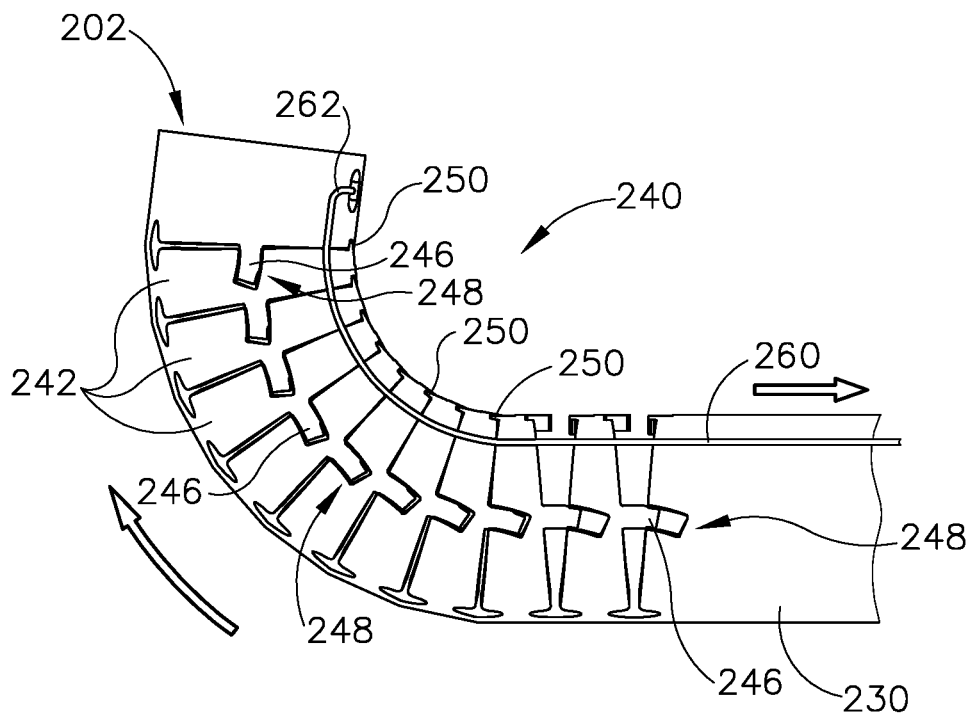
FIG. 3B depicts a cross-sectional side view of the flexible shaft member of FIG. 3A in a bent configuration.

In some versions, both shaft members (210, 230) are formed of a metallic material, such as stainless steel and/or nitinol. In some such versions, shaft members (210, 230) (and at least some other portions of instrument (10)) may be reusable, with such reusable components being subject to cleaning and sterilization between uses on different patients. In some other versions, one or both of shaft members (210, 230) may be formed of a polymeric material. In some such versions, shaft members (210, 230) may be treated as single-use-only components. Flexible shaft member (230) is secured to rigid shaft member (210) and is positioned distally in relation to rigid shaft member (210). As best seen in FIGS. 3A-3B, flexible shaft member (230) includes a flex section (240) that is formed by a series of ribs (242), which are separated by a series of notches (244). Notches (244) are generally V-shaped, with a circular opening at the vertex of each "V." Notches (244) also include tab portions (224) that fit in corresponding sub-notches (226). The top of each "V" includes a set of stop features (222).

As shown in FIG. 3A, when flex section (240) is in a straight configuration, tab portions (224) are disposed in corresponding sub-notches (226) but are not fully seated in sub-notches (226). As also shown in FIG. 3A, when flex section (240) is in a straight configuration, stop features (222) are separated from each other. FIG. 3B shows flex section (240) in a fully deflected (or "bent") configuration. In this state, tab portions (224) are fully seated in sub-notches (226) and stop features (222) are engaged with each other. During the transition between the states shown in FIGS. 3A-3B, tab portions (224) and sub-notches (226) may cooperate to ensure that flex section (240) deflects (or "bends") in a consistent fashion, with sufficient lateral stability; and that flex section (240) provides a consistent and stable deflected or straight state.

By way of example only, flex section (240) may be formed through laser cutting or any other suitable manufacturing process. In some versions, flex section (240) is covered with a flexible wrap (not shown). Such a flexible wrap may prevent tissue and other structures from getting snagged or pinched in notches (244), without compromising the flexibility of flex section (240). A flexible wrap may also ensure that suction provided through guide shaft assembly (200) is focused at a distal end (202) thereof. Various suitable forms that flex section (240) may take will be apparent to those of ordinary skill in the art in view of the teachings herein. By way of further example only, flex section (240) may be constructed and operable in accordance with at least some of the teachings of U.S. Pub. No. 2018/0311472, entitled "Deflectable Guide for Medical Instrument," published Nov. 1, 2018, the disclosure of which is incorporated by reference herein.

Push-pull wire (260) is disposed within shaft members (210, 230) and is operable to provide controlled deflection (or "bending") of flex section (240). As shown in FIGS. 3A-3B, a distal end (262) of push-pull wire (260) is secured to the distal end (232) of flexible shaft member (230), distal to flex section (240). Push-pull wire (260) is disposed near the open tops of the "V" shapes of notches (244). Thus, when push-pull wire (260) is pulled proximally, flex section (240) transitions to a deflected configuration, as shown in FIG. 3B. When push-pull wire (260) is then pushed distally, flex section (240) will return toward a straight configuration. A proximal end (234) of push-pull wire (260), shown in FIG. 2, is secured to cam barrel (270) by a retention key (not shown). Proximal end (234) is threaded into one or more lateral openings in a key recess of cam barrel (270); and then the key is inserted into the key recess to retain proximal end (234) in the lateral openings. Translation of cam barrel (270) drives translation of push-pull wire (260), which in turn causes deflection or straightening of flex section (240) as described above.

Cam barrel (270) is movably coupled with rigid shaft member (210) such that cam barrel (270) is slidable longitudinally along rigid shaft member (210); yet cam barrel (270) is prevented from rotating relative to rigid shaft member (210). As shown in FIG. 2, a tab (212) projects laterally and unitarily from a proximal portion of rigid shaft member (210); and is configured to be slidably received within a lateral channel (272) of cam barrel (270). The fit between tab (212) and lateral channel (272) allows cam barrel (270) to slide longitudinally along rigid shaft member (210) while preventing cam barrel (270) from rotating about rigid shaft member (210). Other suitable structures may be used to achieve this relationship between rigid shaft member (210) and cam barrel (270).

A pair of laterally opposed pins (220), shown in FIG. 2, are configured to be fixedly secured in corresponding openings of deflection control knob (280), and are configured to be movably captured in an annular space (214) defined between annular flanges (116, 118) formed at a proximal end of rigid shaft member (210). The relationship between pins (220) and flanges (216, 218) allows deflection control knob (280) to rotate relative to rigid shaft member (210) while preventing deflection control knob (280) from translating relative to rigid shaft member (210). Other suitable structures may be used to achieve this relationship between rigid shaft member (210) and deflection control knob (280).

As noted above, proximal end (264) of push-pull wire (260) is secured to cam barrel (270), such that push-pull wire (260) translates with cam barrel (270) relative to rigid shaft member (210) in response to rotation of deflection control knob (280) relative to rigid shaft member (210). As also noted above, translation of push-pull wire (260) relative to rigid shaft member (210) causes lateral deflection of flex section (240). The operator may thus selectively deflect flex section (240) by rotating deflection control knob (280) relative to rigid shaft member (210).

When deflection control knob (280) is provided in a first rotational position (e.g., a home position), flex section (240) assumes a straight configuration defining a zero-deflection angle (or "bend angle") relative to the longitudinal axis of guide shaft assembly (200). In this straight configuration, shaft assembly (200) is suitably configured to guide guidewire (302) and dilation catheter (400) into a first anatomical passageway, such as the sphenoid sinus ostium. When deflection control knob (280) is rotated to a second rotational position, flex section (240) may assume a first deflected (or "bent") configuration defining a first deflection angle relative to the longitudinal axis selected to facilitate access to a second anatomical passageway, such as the Eustachian tube. By way of example only, this first deflection angle may be from approximately 50 degrees to approximately 60 degrees, or more particularly at approximately 55 degrees.

When deflection control knob (280) is further rotated to a third rotational position, flex section (240) may assume a second deflected configuration defining a second deflection angle selected to facilitate access to a third anatomical passageway, such as the frontal recess or frontal sinus ostium. By way of example only, this second deflection angle may be from approximately 65 degrees to approximately 70 degrees, or more particularly at approximately 70 degrees. When deflection control knob (280) is further rotated to fourth rotational position, flex section (240) may assume a third deflected configuration defining a third deflection angle selected to facilitate access to a fourth anatomical passageway, such as the maxillary sinus ostium. By way of example only, this third deflection angle may be from approximately 105 degrees to approximately 115 degrees, or more particularly at approximately 110 degrees.

Cam barrel (270) may be configured to lock in place rotationally such that once the operator achieves a desired deflection angle for flex section (240) using deflection control knob (280), flex section (240) may maintain the selected angle until the operator again rotates knob (280). Since guidewire (302) and dilation catheter (402) are slidably disposed within shaft assembly (200), guidewire (302) and dilation catheter (402) will exit the distal end of shaft assembly (200) at whatever deflection angle the operator has selected. In view of the foregoing, an operator may readily achieve various exit angles for guidewire (302) and dilation catheter (402) by rotating deflection control knob (280) relative to rigid shaft member (210). The operator may thus readily dilate various anatomical passageways without having to exchange instruments; and without having to replace pieces of instrument (10).

In addition to enabling deflection of shaft assembly (200) via flex section (240) and deflection control knob (280), it may be further desirable to enable rotation of shaft assembly (200) about its longitudinal axis, to further facilitate access to various anatomical passageways of a patient. In that regard, instrument (10) of the present example further includes a shaft rotation control knob (290) provided on an upper side of handle assembly (100) and which is selectively rotatable to thereby rotate shaft assembly (200) relative to handle assembly (100). In the present version, shaft rotation control knob (290) is oriented such that its rotational axis is perpendicular to the longitudinal axis of shaft assembly (200). In use, an operator may rotate rotation control knob (290) in first and second directions to thereby effect rotation of shaft assembly (200) in corresponding first and second directions about its longitudinal axis. Rotation control knob (290) is suitably positioned on handle assembly (100) such that the operator may rotate knob (290) using the thumb of the same hand that is grasping handle assembly (100).

The various components of dilation instrument (10), including those shown but not described in detail herein, may be configured and operable in accordance with the teachings of U.S. Pub. No. 2019/0015645, entitled "Adjustable Instrument for Dilation of Anatomical Passageway," published Jan. 17, 2019, issued as U.S. Pat. No. 10,874,839 on Dec. 29, 2020; and/or U.S. Pub. No. 2019/0015646, entitled "Adjustable Instrument for Dilation of Anatomical Passageway," published Jan. 17, 2019, issued as U.S. Pat. No. 11,027,105 on Jun. 8, 2021, the disclosures of these references being incorporated by reference herein. Other variations of the features and functionalities described herein will be apparent to those skilled in the art in view of the teachings herein.

II. Exemplary Dilation Instrument with Internal Deflectable Guide Shaft

In some instances, an operator may wish to use an internal guide rail or shaft to guide a dilation catheter like dilation catheter (402); instead of using an external guide catheter or shaft like shaft assembly (200) to guide a dilation catheter like dilation catheter (402). In some instruments, an internal guide or shaft may be used as a probe or seeker device in a way that an external guide could not be used. An example of an instrument with an internal guide is described in U.S. Pat. No. 10,137,286, entitled "Apparatus for Bending Malleable Guide of Surgical Instrument," issued Nov. 27, 2018, the disclosure of which is incorporated by reference herein. While the instrument described in that reference includes an internal guide that can be used as a seeker and also as a guide for a translating guide catheter, the instrument requires the use of an additional, separate device in order to bend the internal guide to achieve a preferred guide angle. This may require the use of at least one additional hand in order to accomplish the guide bending procedure. Moreover, this would require the instrument to be completely removed from the patient in order to accomplish the guide bending procedure, followed by re-insertion of the instrument into the patient.

In view of the foregoing, it may be desirable to provide a variation of dilation instrument (10) that provides the enhanced functionality associated with an internal guide like the guide disclosed in U.S. Pat. No. 10,137,286; while enabling the operator to achieve the same kind of selective bending of the guide in a manner similar to that provided through dilation instrument (10). The following describes merely illustrative examples dilation instruments (110, 900) that provide the advantages of an internal guide and the advantages of facilitated control over bending of the guide.

A. Dilation Instrument with Translating Deflection Actuation Assembly

Figure 4:
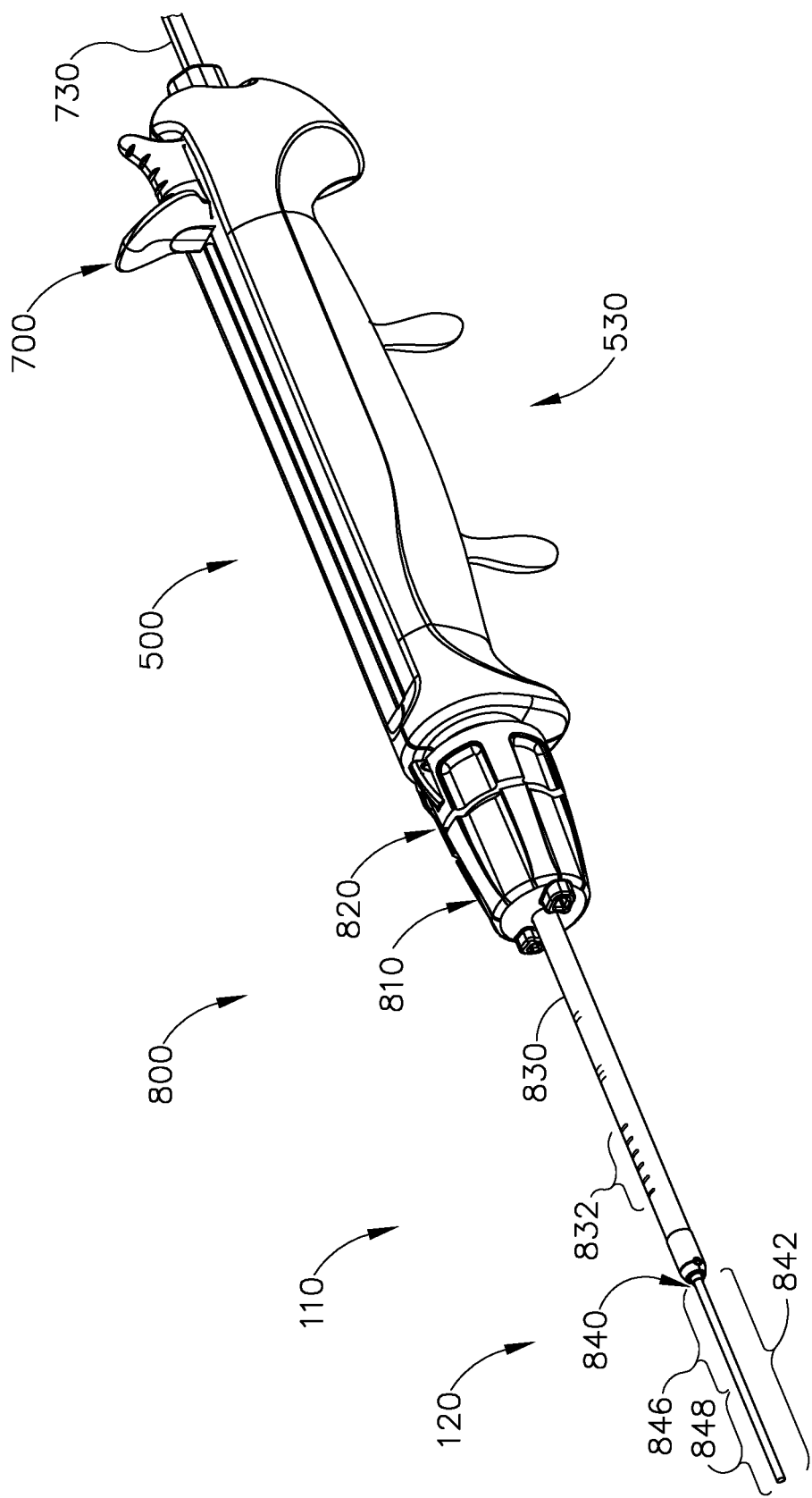
FIG. 4 depicts a perspective view of an exemplary alternative dilation instrument.
Figure 5B:
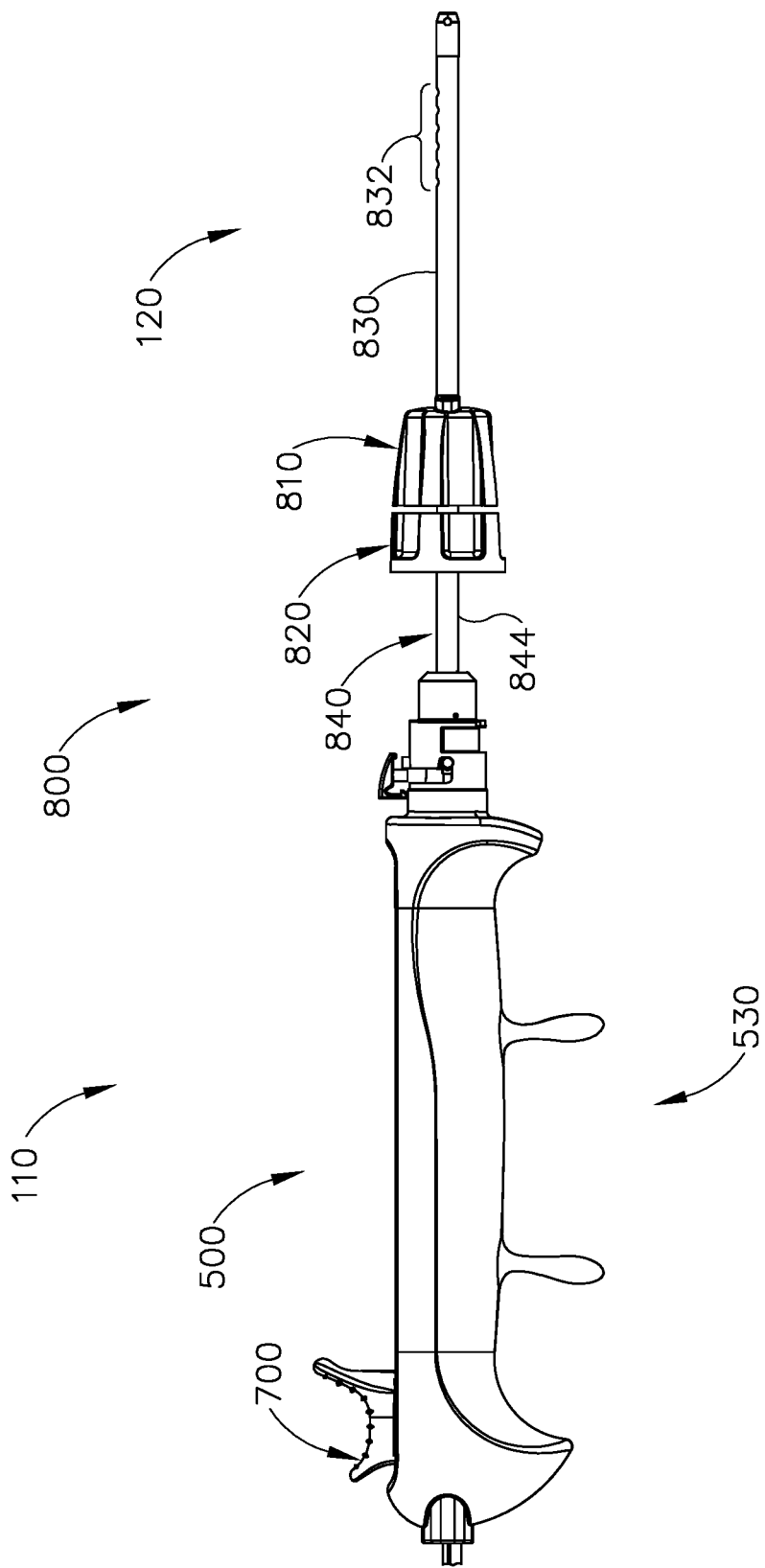
FIG. 5B depicts a side view of the dilation instrument of FIG. 4, with the deflection actuation assembly in a distal position and in a non-actuated state, and with the guide shaft in the straight configuration.
Figure 5C:
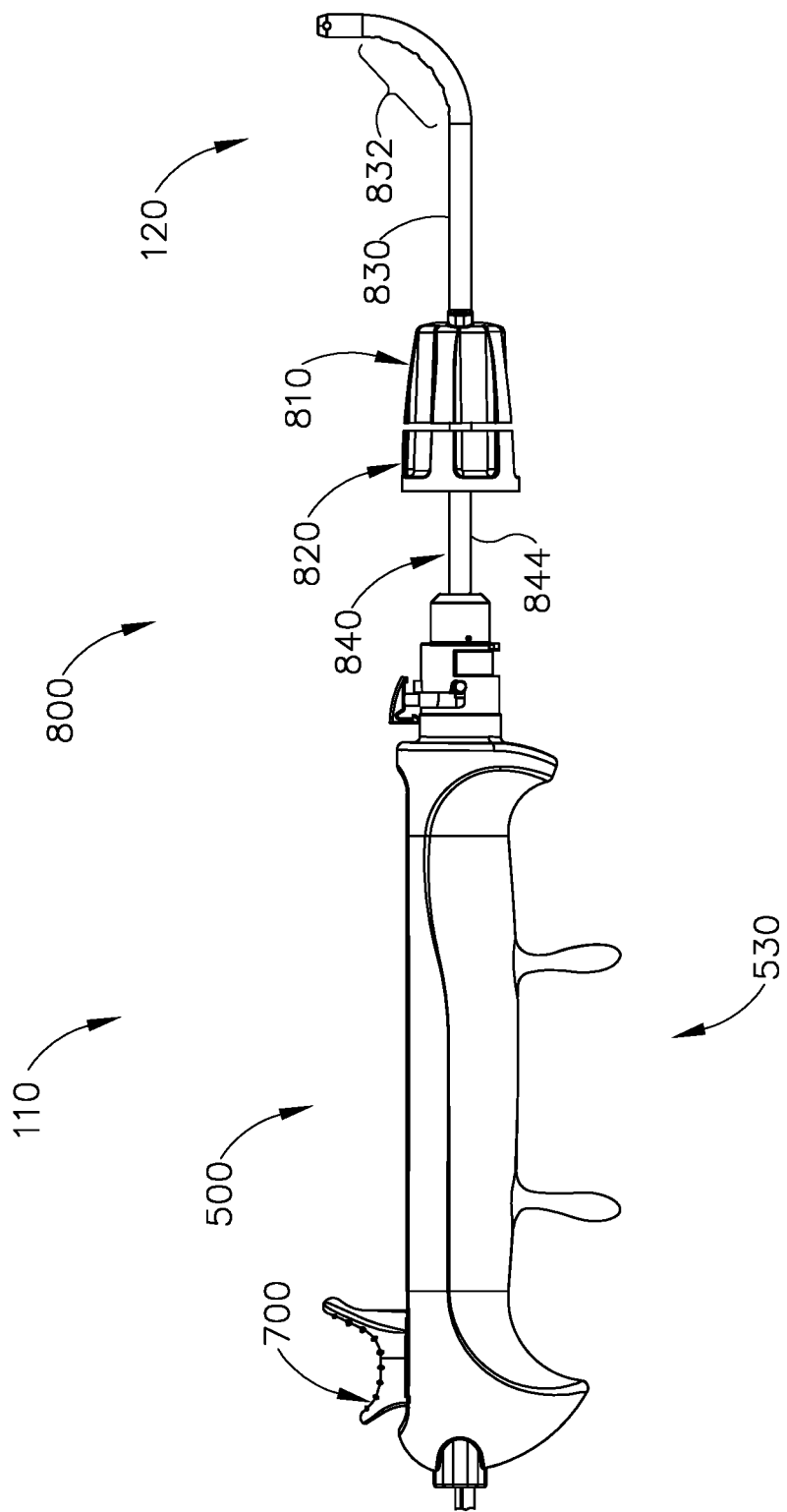
FIG. 5C depicts a side view of the dilation instrument of FIG. 4, with the deflection actuation assembly in the distal position and in an actuated state, and with the guide shaft being bent by the actuated deflection actuation assembly.
Figure 5D:
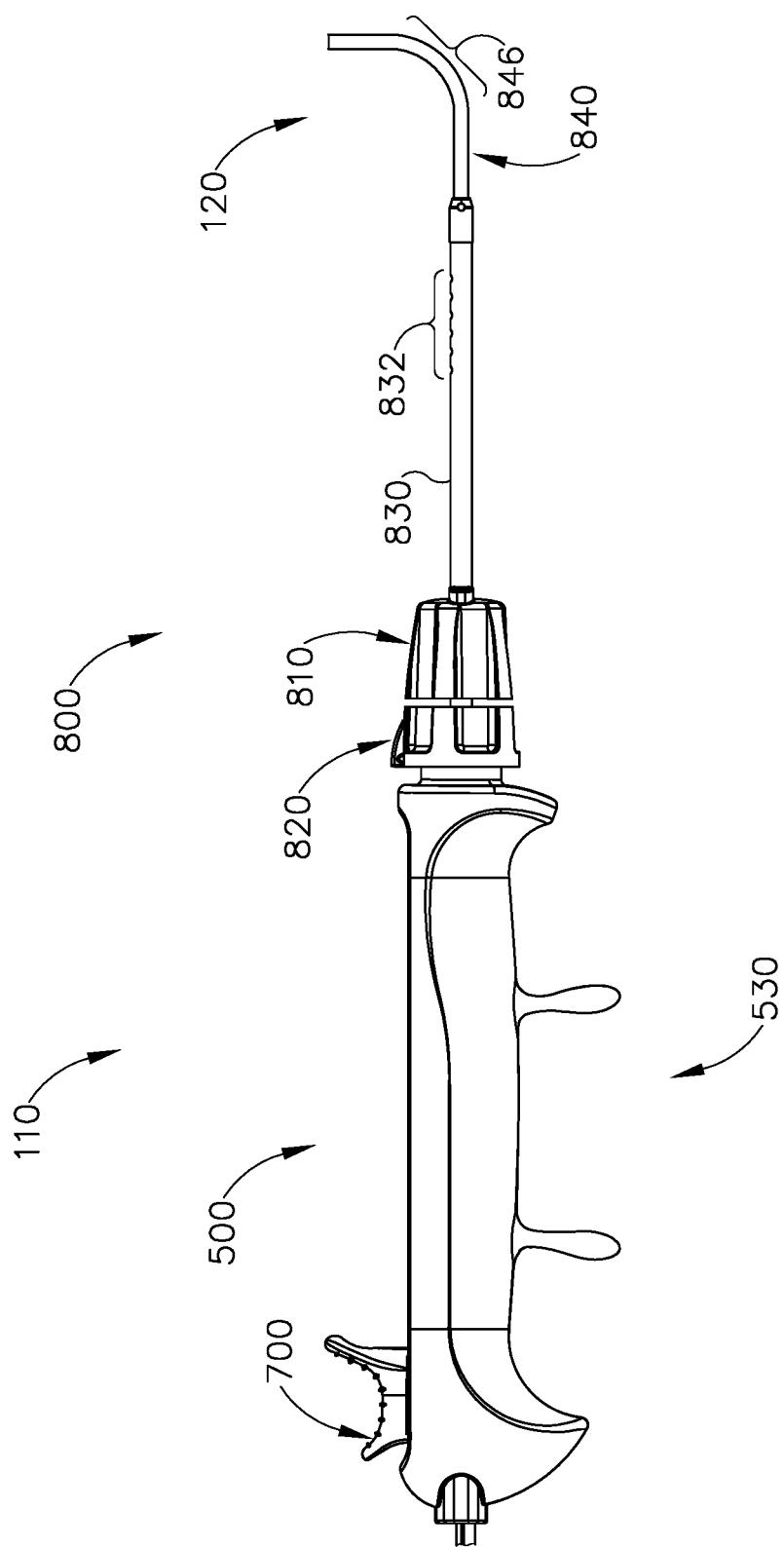
FIG. 5D depicts a side view of the dilation instrument of FIG. 4, with the deflection actuation assembly in the proximal position and the guide shaft left in the bent state of FIG. 5C.
Figure 5E:
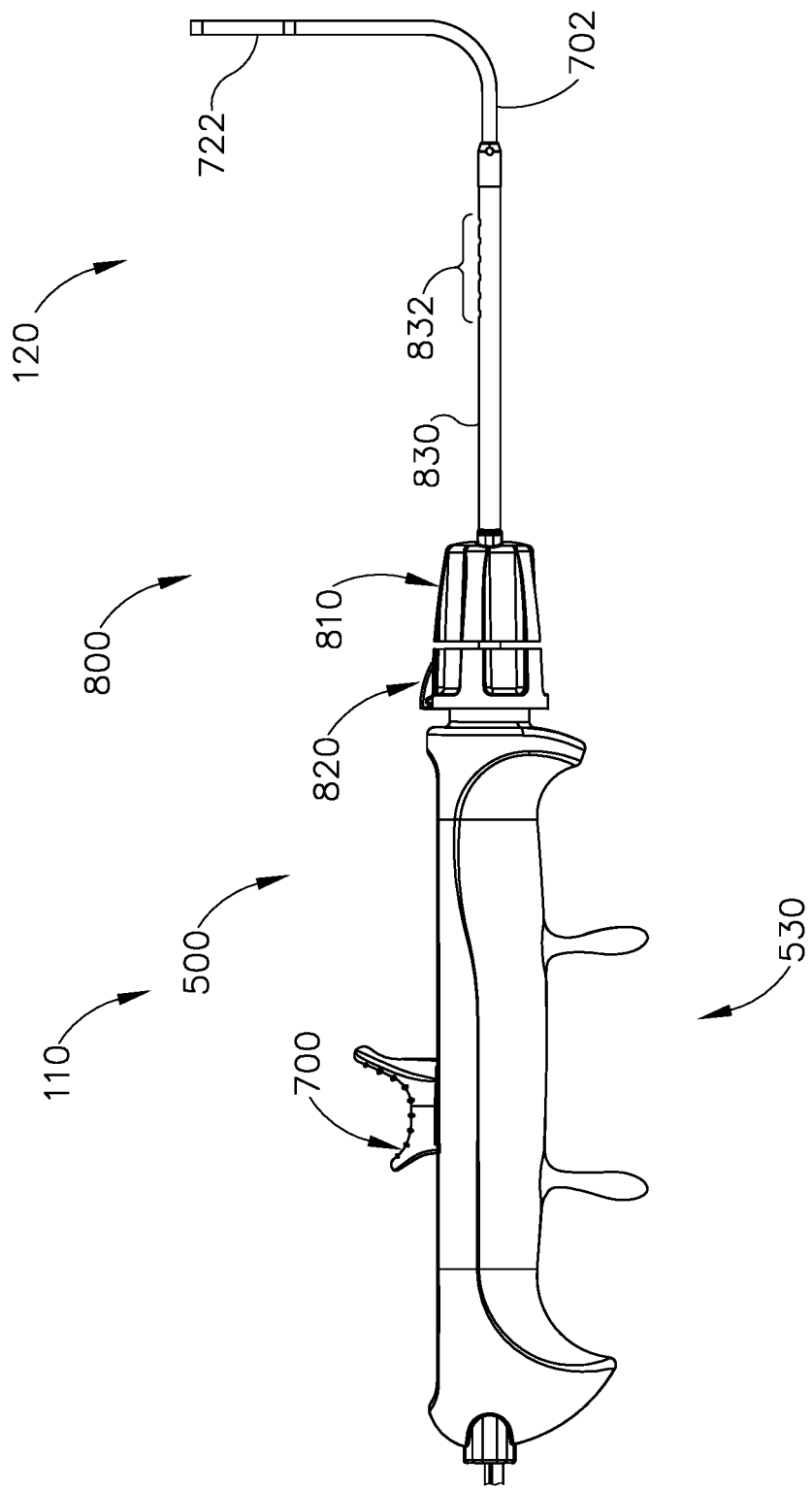
FIG. 5E depicts a side view of the dilation instrument of FIG. 4, with the deflection actuation assembly in the proximal position and the guide shaft left in the bent state of FIG. 5C, with a dilation catheter advanced to a distal position along the bent guide shaft, and with a dilator of the dilation catheter in a non-expanded state.
Figure 5F:
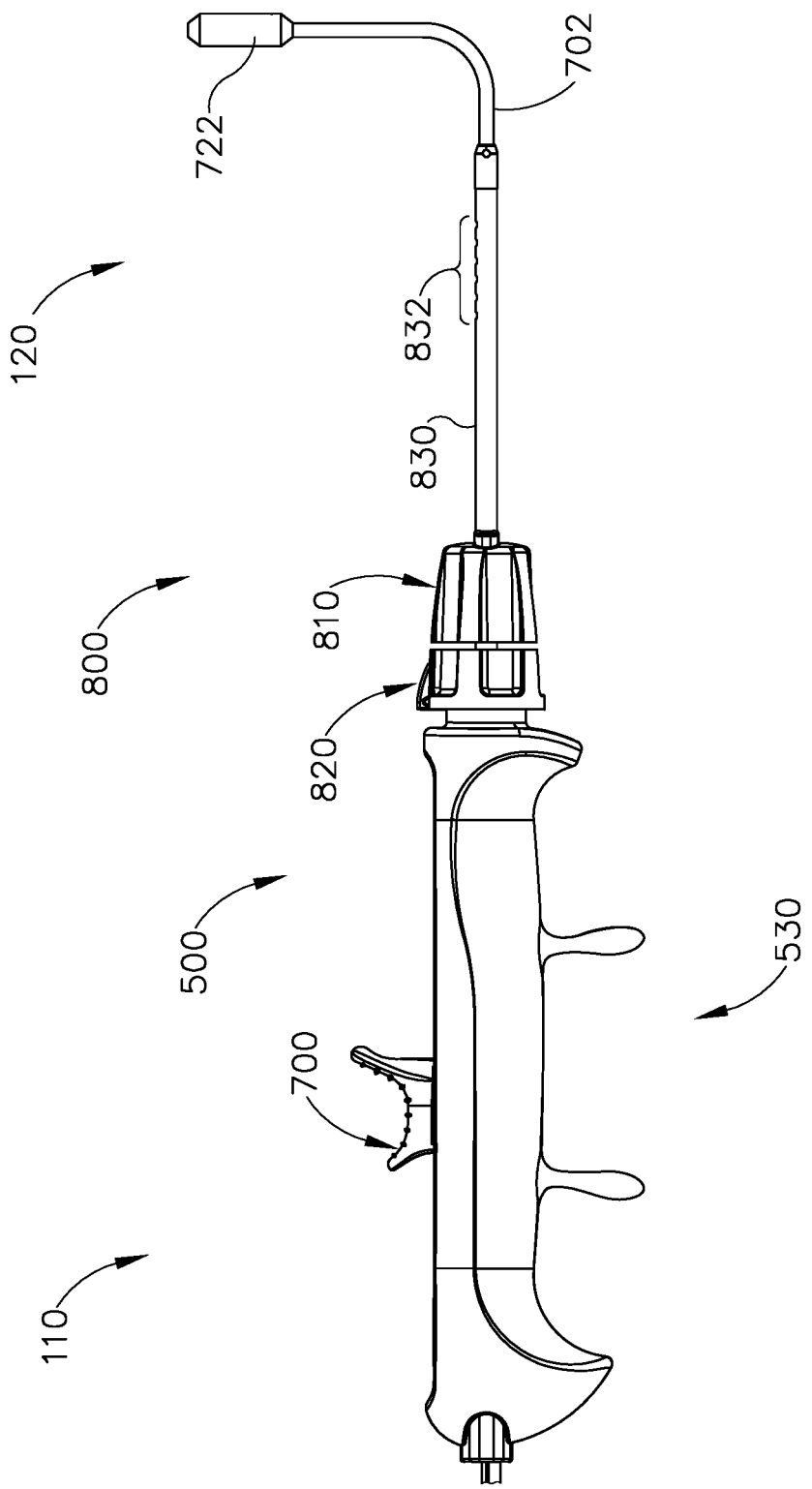
FIG. 5F depicts a side view of the dilation instrument of FIG. 4, with the deflection actuation assembly in the proximal position and the guide shaft left in the bent state of FIG. 5C, with a dilation catheter advanced to a distal position along the bent guide shaft, and with a dilator of the dilation catheter in an expanded state.

As shown in FIGS. 4-5F, dilation instrument (110) of the present example includes a handle assembly (500) defining main body for dilation instrument (110) and a shaft assembly (120) distally extending from a distal end of handle assembly (500). Shaft assembly (120) includes a malleable guide shaft (840), which includes a rigid portion (844) positioned nearest handle assembly (500), and a guide rail region (842) at the distal end guide shaft (840). Guide rail region (842) includes a malleable portion (846), which is distal to proximal rigid portion (844), and a rigid portion (848) that is distal to malleable portion (846). Handle assembly (500) also includes a grip portion (530) to facilitate grasping and control of dilation instrument (110) and related functions. Grip portion (50) may be selectively removable from dilation instrument (110) in some versions.

Dilation instrument (110) further includes a deflection actuation assembly (800) that is positioned distally in relation to grip portion (530) and that is operable to selectively deflect guide rail region (842) of guide shaft (840) laterally relative to the longitudinal axis of shaft assembly (120). Deflection actuation assembly (800) is configured to translate longitudinally, as a unit, along guide shaft (840). Deflection actuation assembly (800) of this example includes a proximal stationary knob (820), an adjacently positioned distal rotary knob (810), and an outer shaft (830) projecting distally from knobs (820). Outer shaft (830) is coaxially and slidably disposed about the outer perimeter of the guide shaft (840). Outer shaft (830) and rigid proximal portion (844) of shaft assembly (120) may include interacting features (e.g., key and keyway, mating hex features, etc.) allowing the outer shaft (830) to slide along the rigid proximal portion (844) while preventing the outer shaft (830) from rotating about the rigid proximal portion (844).

The distal portion of outer shaft (830) includes a deflectable region (832) that is driven by rotary knob (810). As described in greater detail below, when rotary knob (810) is actuated to drive deflectable region (832) to a deflected state, the deflection of deflectable region (832) may drive guide rail region (842) of guide shaft (840) to a deflected state. Deflection actuation assembly (800) may incorporate features similar to those described above with reference to FIGS. 2-3B to cause the lateral deflection of deflectable region (832) relative to the longitudinal axis of shaft assembly (120) in response to rotation of rotary knob (810) relative to stationary knob (820). For instance, the rotation of rotary knob (810) relative to stationary knob (820) about the longitudinal axis defined by the guide shaft (840) may deflect deflectable region (832) with applied tension through a push-pull wire similar to push-pull wire (260) described above.

When rotary knob (810) is released, this may release tension in the push-pull wire, such that deflectable region (832) no longer applies a bending force to guide rail region (842) of guide shaft (840) and is capable of returning to a straight configuration. Therefore, when outer shaft (830) is no longer experiencing tension from the push-pull wire, outer shaft (830) can be translated along guide shaft (840) without causing deflection of guide rail region (842) either toward or away from the longitudinal axis. It should also be noted that guide shaft (840) is configured to remain deflected after deactivation of deflection actuation assembly (800) when deflection actuation assembly (800) is located at the distal position. While knobs (810, 820) are provided in the present example, deflection actuation assembly (800) may use any other kinds of actuators in addition to or in lieu of knobs (810, 820) to drive a push-pull wire or other actuation feature to controllably deflect deflectable region of outer shaft (830). Various alternative structures and configurations will be apparent to those skilled in the art in view of the teachings herein.

Directable region (832) may be configured to only bend when positioned over flexible region (846) of guide shaft (840) after deflection actuation assembly (800) has been translated along the guide shaft (840). The alignment of directable region (832) and flexible region (846) may be simplified by causing the alignment to be made when deflection actuation assembly (800) is fully translated distally from the handle assembly (500). The deflection of directable region (832) and flexible region (846) is contemplated to be in any direction away from the longitudinal axis in any direction needed during a procedure.

Dilation instrument (110) of the present example further includes a dilation catheter slider (700) that slidably coupled with grip portion (530) and is operable to translate a dilation catheter (702). Dilation catheter (702) is slidably disposed over guide shaft (840) and inside the inner diameter of outer shaft (830). As dilation catheter (702) translates distally, dilation catheter (702) will follow the path defined by guide rail region (842) of guide shaft (840). The proximal end (730) of dilation catheter (702) may be coupled with any suitable fluid source or fluid sources, such as inflation fluid source (14) and an irrigation fluid source (16) described above. As shown in FIGS. 5E-5F, the distal end of dilation catheter (702) includes an expandable dilator (722), which is in the form of a balloon in the present example. Dilator (722) is configured to expand when filled with fluid (e.g., saline) from a fluid source that is coupled with proximal end (730) of dilation catheter (702).

While not shown, some versions of dilation instrument (110) may comprise a guidewire (602) slidably disposed within the inner diameter of outer shaft (830); or more particularly within an inner diameter of guide shaft (840). Dilation instrument (110) may also include a guidewire actuation assembly, similar to guidewire actuation assembly (300) of instrument (10), that is operable to translate the guidewire along a longitudinal axis and rotate the guidewire about the longitudinal axis. Some versions of dilation instrument (110) may also include a shaft rotation assembly (not shown) that is operable to rotate the entire shaft assembly (120) unitarily relative to handle assembly (500) about a longitudinal axis. Various suitable forms that such a shaft rotation assembly may take will be apparent to those skilled in the art in view of the teachings herein.

FIGS. 5A-5F show an exemplary sequence of operation of dilation instrument (110). As shown in FIG. 5A, dilation instrument (110) is in a state where dilation catheter slider (700), dilation catheter (702), and deflection actuation assembly (800) are in proximal positions. In this configuration, guide rail region (842) of guide shaft (840) is exposed relative to the distal end of outer shaft (830) and is in a straight configuration. In some instances, guide rail region (842) may be inserted into a patient's head (e.g., via a nostril or via the mouth) when dilation instrument (110) is in the state shown in FIG. 5A.

As shown in FIG. 5B, deflection actuation assembly (800) has translated distally along the longitudinal axis defined by guide shaft (840) over guide shaft (840), to a position where deflectable region (832) of outer shaft (830) is longitudinally aligned over malleable distal portion (846) of guide shaft (840). As shown in FIG. 5C, rotary knob (810) of deflection actuation assembly (800) is rotated relative to stationary knob (820), thereby bending deflectable region (832) of outer shaft (830) laterally away from the longitudinal axis. As outer shaft (830) is bent at deflectable region (832), malleable distal portion (846) is also bent such that guide rail region (842) is deflected away from the axis by deflectable region (832).

While FIG. 5C shows deflectable region (832) and guide rail region (842) bent to an angle of approximately 90 degrees, it should be understood that deflection actuation assembly (800) may instead be actuated to bend guide rail region (842) at various other bend angles, including angles greater than 90 degrees and angles less than 90 degrees. The selected bend angle may correspond with the particular anatomical passageway that the operator wishes to dilate with dilator (722), as is known in the art. It should also be understood that knobs (810, 820) may include detents, visual indicia, and/or other features to provide feedback to the operator, indicating the bend angle of deflectable region (832) and guide rail region (842) as the operator rotates rotary knob (810) relative to stationary knob (820).

Once the operator has achieved the desired bend angle in guide rail region (842), the operator may release rotary knob (810) and then translate deflection actuation assembly (800) back to the proximal position as shown in FIG. 5D, leaving bent guide rail region (842) exposed. With the release of rotary knob (810), outer shaft (830) enters a relaxed stated where it is no longer forced to be bent. As deflection actuation assembly (800) is retracted to the proximal position, outer shaft (830) eventually straightens out along rigid portion (844) of guide shaft (840); while guide rail region (842) maintains the bent configuration due to the malleability of distal portion (846). As deflection actuation assembly (800) is retracted to the proximal position and outer shaft (830) correspondingly straightens out, rotary knob (810) may rotate freely relative to stationary knob (820) to relieve tension in the push-pull wire or other actuator that had driven deflectable region (832) to the bent state. It should be noted that any one or more of the steps depicted in FIGS. 5B-5D may be carried out before guide rail region (842) is disposed in the patient's head or after guide rail region (842) has been positioned in the patient's head. In any case, the operator may manipulate dilation instrument to position the distal end of bent guide rail region (842) to thereby orient the distal end of bent guide rail region (842) toward the anatomical passageway (e.g., paranasal sinus ostium, frontal recess, Eustachian tube, etc.) that the operator wishes to dilate.

After the operator has achieved the desired bend angle in guide rail region (842) and retracted deflection actuation assembly (800) to expose guide rail region (842), the operator may slide dilation catheter slider (700) distally along grip portion (530) to thereby drive dilation catheter (702) distally along guide rail region (842), as shown in FIG. 5E. Due to the malleability of distal portion (846) of guide shaft (840), guide rail region (842) fully maintains its bent configuration as dilation catheter (702) translates along guide rail region (842). As dilation catheter (702) translates distally along guide rail region (842), dilator (722) eventually passes the distal end of guide rail region (842) and enters the targeted anatomical passageway. Dilator (722) remains in a non-expanded configuration until dilator (722) is positioned within the targeted anatomical passageway. Once dilator (722) is positioned within the targeted anatomical passageway, fluid may be communicated to dilator (722) via proximal end (730) of dilation catheter (702), thereby expanding dilator (722) as shown in FIG. 5F. In the expanded state, dilator (722) may dilate the anatomical passageway in which dilator (722) is disposed.

After dilator (722) has dilated the targeted anatomical passageway, fluid may be relieved or withdrawn from dilator (722) to return dilator (722) to the non-expanded configuration shown in FIG. 5E. The operator may then retract dilation catheter slider (700) proximally along grip portion (530) to thereby drive dilation catheter (702) proximally to the position shown in FIG. 5D. In some cases, dilation instrument (110) may simply be removed from the head of the patient at this stage, even while guide rail region (842) is in a bent state.

Alternatively, after dilator (722) has returned to the non-expanded configuration shown in FIG. 5E, the operator may drive deflection actuation assembly (800) distally to the position shown in FIG. 5C, then rotate rotary knob (810) relative to stationary knob (820). In some such cases, the operator may wish to rotate rotary knob (810) relative to stationary knob (820) to drive deflectable region (832) of outer shaft (830) to a straight configuration, thereby driving guide rail region (842) to a straight configuration, before removing dilation instrument (110) from the head of the patient. In some other cases, the operator may wish to rotate rotary knob (810) relative to stationary knob (820) to drive deflectable region (832) of outer shaft (830) to a second bent configuration, thereby driving guide rail region (842) to a second bent configuration. This second bent configuration may reorient guide rail region (842) to a second bend angle that is selected to facilitate access to a second anatomical structure in the head of the patient. After achieving this second bend angle, the above-described steps may be repeated to dilate the second anatomical structure. This process may be repeated as many times as desired, such that guide rail region (842) may be bent two or more times to guide dilation catheter (702) into two or more anatomical structures within the head of the patient, without needing to remove dilation instrument (110) from the head of the patient between these dilations.

B. Dilation Instrument with Non-Translating Deflection Actuation Assembly

Figure 6A:
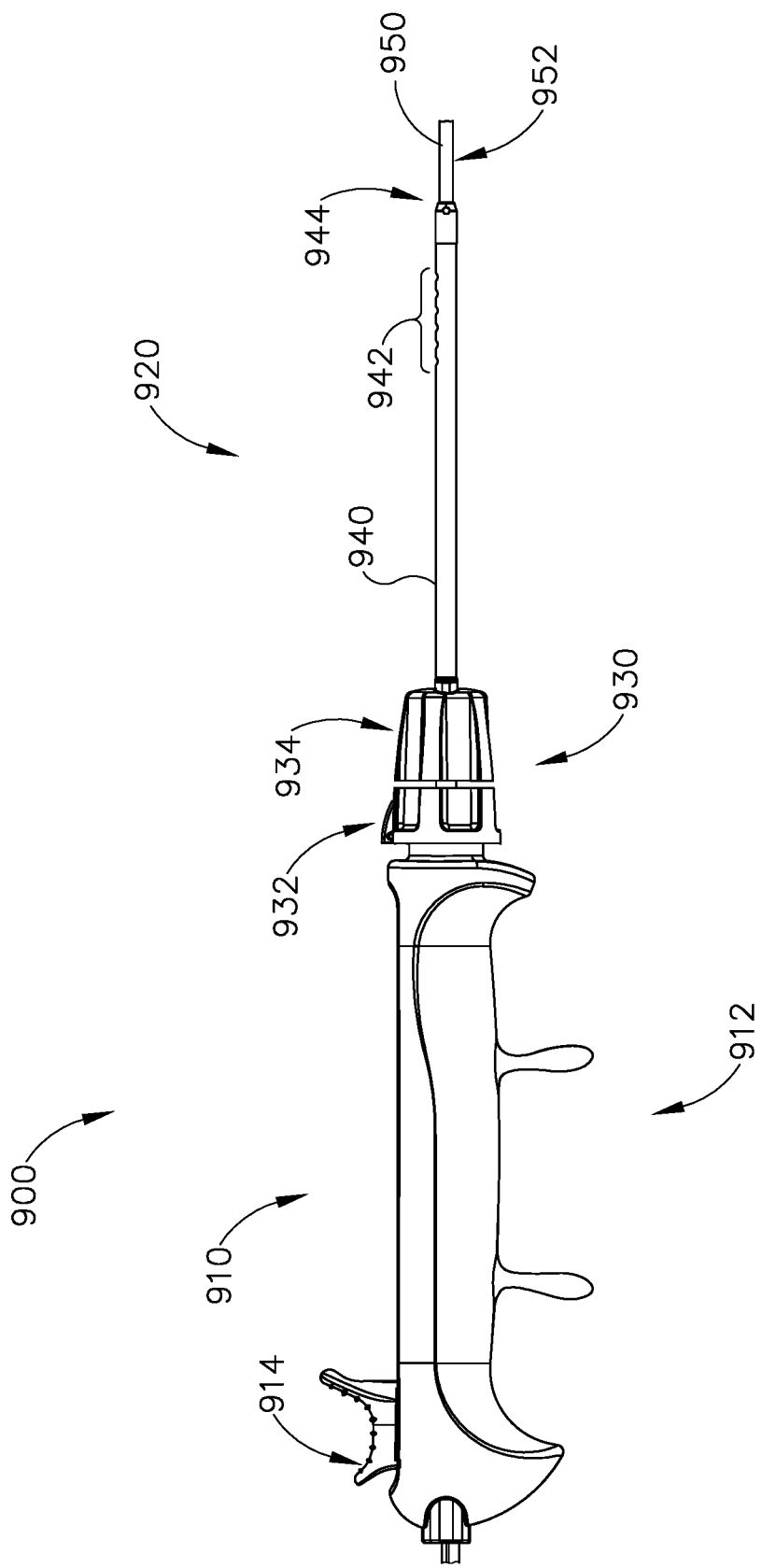
FIG. 6A depicts a side view of another example of a dilation instrument, with shaft assembly in a straight configuration.
Figure 6B:
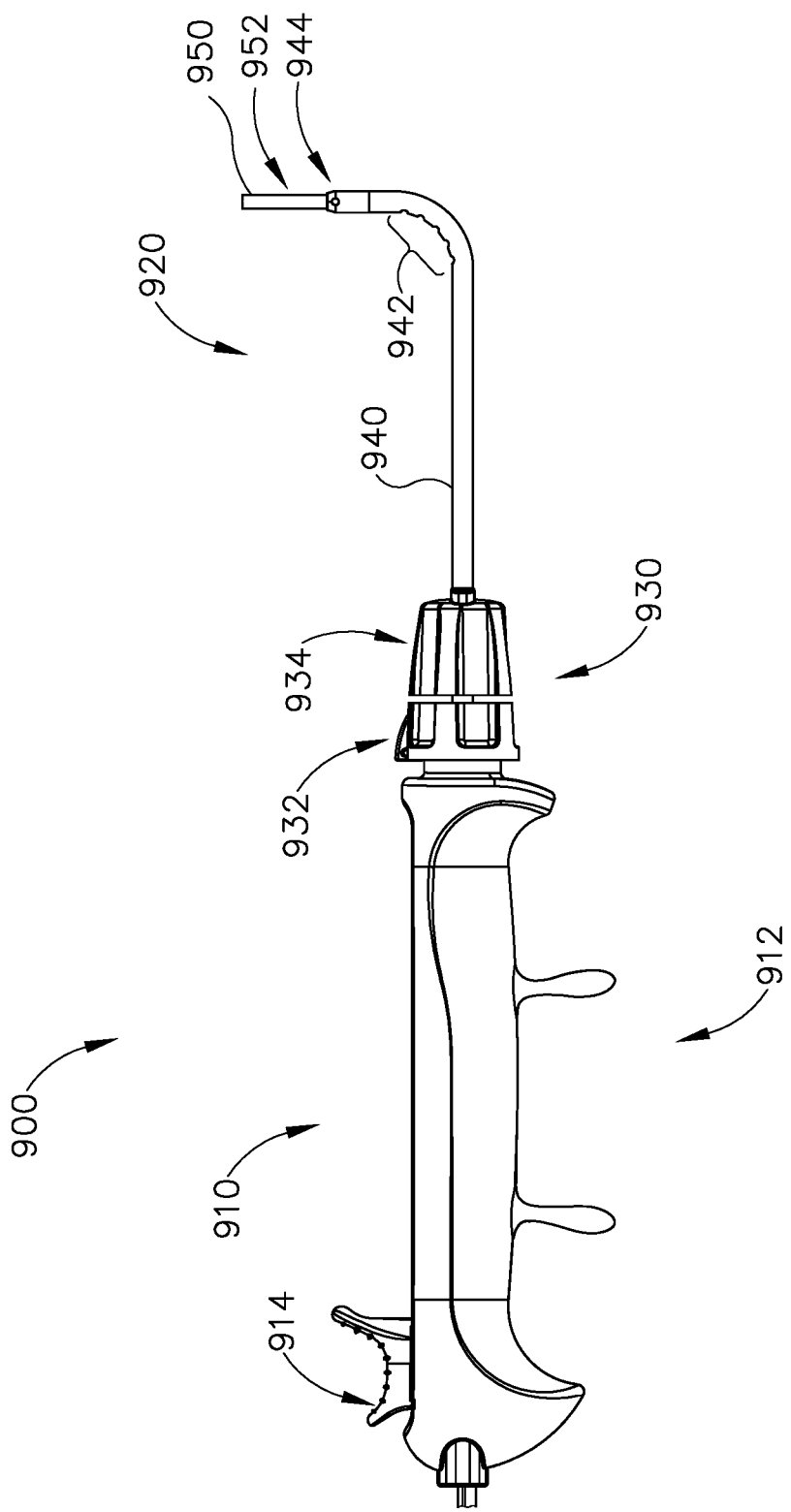
FIG. 6B depicts a side view of the dilation instrument of FIG. 6A, with the shaft assembly in a bent configuration.

FIGS. 6A-6B show another dilation instrument (900) that is substantially similar to dilation instrument (110) except for the differences described below. Dilation instrument (900) of this example includes a handle assembly (910) with a grip portion (912) and a dilation catheter slider (914), just like grip portion (530) and dilation catheter slider (700)

described above. Dilation instrument (900) further includes a shaft assembly (920) and a deflection actuation assembly (930).

Shaft assembly (920) includes an outer shaft (940) and an inner shaft (950). In the present example, shafts (940, 950) are longitudinally fixed relative to each other, such that outer shaft (940) does not longitudinally translate relative to inner shaft (950). Outer shaft (940) includes a flexible section (942) that is operationally coupled with deflection actuation assembly (930).

Deflection actuation assembly (930) includes a first knob (932) and a second knob (934). Second knob (934) is rotatable relative to first knob (932) to transition flexible section (942) between a straight configuration (FIG. 6A) and a bent configuration (FIG. 6B). By way of example only, deflection actuation assembly (930) may be coupled with flexible section (942) or the distal end (944) of outer shaft (940) via one or more pull-wires. In such versions, rotation of second knob (934) relative to first knob (932) may pull such one or more pull-wires, which may in turn drive lateral deflection of flexible section (942) and distal end (944) from the straight configuration shown in FIG. 6A to a bent configuration like what is shown in FIG. 6B. In some such versions, flexible section (942) is resiliently biased to return to the straight configuration, such that outer shaft (940) will return to the straight configuration when tension is relieved in the one or more pull-wires when second knob (934) is rotated in the opposite direction relative to first knob (932). Alternatively, the one or more pull-wires may have sufficient column strength to push, such that the one or more pull-wires may actively drive outer shaft (940) to return to the straight configuration when second knob (934) is rotated in the opposite direction relative to first knob (932). In such versions, flexible section (942) may simply be passively flexible rather than being resiliently biased toward the straight configuration. As yet another merely illustrative variation, flexible section (942) may be malleable such that flexible section (942) will maintain a bend angle that is applied by deflection actuation assembly (930); while also allowing deflection actuation assembly (930) to drive flexible section (942) back to the straight configuration.

Inner shaft (950) may be configured and operable like malleable guide shaft (840) described above. Inner shaft (950) of this example includes a rigid distal portion (952) that protrudes distally relative to distal end (944) of outer shaft (940). Inner shaft (950) also includes a flexible portion (not shown) that is longitudinally positioned within flexible section (942) of outer shaft (940). In some versions, this flexible portion of inner shaft (950) is malleable, such that the malleability of the flexible portion of inner shaft (950) will maintain the bend angle formed in the flexible portion of inner shaft (950). Such malleability of the flexible portion of inner shaft (950) may provide sufficient strength to resist a resilient bias of flexible section (942) of outer shaft (940) to return to the straight configuration in versions where flexible section (942) of outer shaft (940) is resiliently biased to return to the straight configuration. In versions where flexible section (942) of outer shaft (940) is not resiliently biased to return to the straight configuration, a malleable flexible portion of inner shaft (950) may still be driven by deflection actuation assembly (930) return to a straight configuration after being driven to a bent configuration. In some other variations, the flexible portion of inner shaft (950) is passively flexible rather than being malleable. In such versions, a malleable version of flexible section (942) of outer shaft (940) may provide the support to maintain a bend angle as shown in FIG. 6B. Alternatively, the flexible portion of inner shaft (950) and flexible section (942) of outer shaft (940) may both be passively flexible; and deflection actuation assembly (930) may include one or more features to maintain a bend angle as shown in FIG. 6B. By way of example only, deflection actuation assembly (930) may include self-locking threading, detent features, locking features, or any other suitable kinds of features as will be apparent to those skilled in the art in view of the teachings herein.

In the present example, the dilation catheter (not shown) of dilation instrument (900) is radially interposed between the inner diameter of outer shaft (940) and the outer diameter of inner shaft (950). The dilation catheter of dilation instrument (900) is thus positioned similar to dilation catheter (702) of dilation instrument (110). Also like dilation catheter (702) of dilation instrument (110), the dilation catheter of dilation instrument (900) is coupled with dilation catheter slider (914), such that dilation catheter slider (914) may be advanced distally relative to grip portion (912) to thereby drive the dilation catheter distally relative to outer shaft (940) and inner shaft (950). Dilation instrument (900) may thus achieve operational states similar to the operational states of dilation instrument (110) shown in FIGS. 5E-5F. In some other variations, the dilation catheter of dilation instrument (900) is slidably disposed about the exterior of outer shaft (940) and inner shaft (950). In such versions, the dilation catheter of dilation instrument (900) is not positioned within the interior of outer shaft (940). In versions where the dilation catheter of dilation instrument (900) is slidably disposed about the exterior of outer shaft (940) and inner shaft (950), dilation catheter slider (914) may still be used to advance the dilation catheter distally in the manner described above; and the dilation catheter may still be used to dilate a paranasal sinus ostium, Eustachian tube, or other passageway in a patient's ear, nose, or throat as described above.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a body; (b) a first shaft extending distally relative to the body, wherein the first shaft includes a malleable distal portion; (c) an actuation assembly, wherein the actuation assembly includes: (i) second shaft extending distally relative to the body, wherein the second shaft is coaxially positioned about the first shaft, and (ii) an actuator, wherein the actuator is operable to selectively bend the malleable distal portion of the first shaft; and (d) a dilation catheter coaxially interposed between the first shaft and the second shaft, wherein the dilation catheter includes an expandable dilator, wherein the dilation catheter is operable to translate along the malleable distal portion of the first shaft.

Example 2

The apparatus of Example 1, wherein the first shaft includes a rigid proximal portion.

Example 3

The apparatus of any one or more of Examples 1 through 2, wherein the second shaft includes a deflectable distal portion, wherein the deflectable distal portion is operable to bend the malleable distal portion of the first shaft in response to actuation of the actuator.

Example 4

The apparatus of Example 3, wherein the actuation assembly is operable to translate along the first shaft between a proximal position and a distal position, wherein the deflectable distal portion of the second shaft is configured to be positioned proximal to the malleable distal portion of the first shaft when the actuation assembly is in the proximal position, wherein the deflectable distal portion of the second shaft is configured to be positioned about the malleable distal portion of the first shaft when the actuation assembly is in the distal position.

Example 5

The apparatus of any one or more of Examples 1 through 4, wherein the actuator is positioned at a proximal end of the second shaft.

Example 6

The apparatus of Example 5, wherein the actuator is positioned distal to the body.

Example 7

The apparatus of any one or more of Examples 1 through 6, wherein the actuation assembly is operable to translate relative to the body along the first shaft.

Example 8

The apparatus of any one or more of Examples 1 through 7, wherein the actuator comprises a first member and a second member, wherein the first member is rotatable relative to the second member to selectively bend the malleable distal portion of the first shaft.

Example 9

The apparatus of Example 8, wherein the first member comprises a rotary knob rotatable relative to the second shaft, wherein the second member comprises a stationary knob fixedly secured relative to the second shaft.

Example 10

The apparatus of any one or more of Examples 8 through 9, wherein the actuator further comprises a translating member, wherein the translating member is configured to translate and thereby selectively bend the malleable distal portion of the first shaft in response to rotation of the first member relative to the second member.

Example 11

The apparatus of Example 10, wherein the translating member comprises a wire.

Example 12

The apparatus of any one or more of Examples 1 through 11, wherein first shaft and the actuation assembly include features configured to prevent rotation of the second shaft relative to the first shaft.

Example 13

The apparatus of any one or more of Examples 1 through 12, further comprising a slider slidably coupled with the body, wherein the slider is operable to drive the dilation catheter longitudinally along the first shaft.

Example 14

The apparatus of any one or more of Examples 1 through 13, wherein the dilator in a non-expanded state is configured to fit in an anatomical passageway in a human head, wherein the dilator in an expanded state is configured to dilate the anatomical passageway.

Example 15

The apparatus of any one or more of Examples 1 through 14, wherein the dilation catheter is operable to translate between a proximal position and a distal position, wherein the dilator is configured to be positioned distal to a distal end of the first shaft when the dilation catheter is in the distal position.

Example 16

The apparatus of Example 15, wherein the dilator is configured to be positioned proximal to a distal end of the second shaft when the dilation catheter is in the proximal position.

Example 17

An apparatus, comprising: (a) a body; (b) a shaft assembly extending distally relative to the body, wherein the shaft assembly comprises: (i) a first shaft, wherein the first shaft includes a malleable distal portion, and (ii) a second shaft, wherein the second shaft is coaxially positioned about the first shaft, wherein the second shaft includes a deflectable portion; (c) an actuator, wherein the actuator is operable to selectively drive the deflectable portion to bend the malleable distal portion of the first shaft; and (d) a dilation catheter coaxially interposed between the first shaft and the second shaft, wherein the dilation catheter includes an expandable dilator, wherein the dilation catheter is operable to translate along the malleable distal portion of the first shaft.

Example 18

The apparatus of Example 17, wherein the actuator is secured to a proximal portion of the second shaft.

Example 19

A method comprising: (a) advancing an outer shaft of a dilation instrument distally along an inner shaft of the dilation instrument to thereby position a deflectable portion of the outer shaft along a malleable portion of the inner shaft; (b) actuating an actuator of the dilation instrument to drive the deflectable portion of the outer shaft to bend the malleable portion of the inner shaft laterally; and (c) retracting the outer shaft proximally relative to the inner shaft, wherein the malleable portion of the inner shaft remains bent after the outer shaft is retracted proximally.

Example 20

The method of Example 19, further comprising advancing a dilation catheter distally along the inner shaft, wherein the dilation catheter is coaxially interposed between the inner shaft and the outer shaft, wherein the dilation catheter is advanced distally along the malleable portion of the inner shaft, wherein the malleable portion of the inner shaft remains bent as the dilation catheter is advanced distally along the malleable portion of the inner shaft.

IV. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An apparatus, comprising:
(a) a body;
(b) a first shaft extending distally relative to the body, wherein the first shaft includes a malleable distal portion;
(c) an actuation assembly, wherein the actuation assembly includes:
(i) second shaft extending distally relative to the body, wherein the second shaft is coaxially positioned about the first shaft, and
(ii) an actuator, wherein the actuator is operable to selectively bend the malleable distal portion of the first shaft; and
(d) a dilation catheter coaxially interposed between the first shaft and the second shaft, wherein the dilation catheter includes an expandable dilator, wherein the dilation catheter is operable to translate along the malleable distal portion of the first shaft.

2. The apparatus of claim 1, wherein the first shaft includes a rigid proximal portion.

3. The apparatus of claim 1, wherein the second shaft includes a deflectable distal portion, wherein the deflectable distal portion is operable to bend the malleable distal portion of the first shaft in response to actuation of the actuator.

4. The apparatus of claim 3, wherein the actuation assembly is operable to translate along the first shaft between a proximal position and a distal position, wherein the deflectable distal portion of the second shaft is configured to be positioned proximal to the malleable distal portion of the first shaft when the actuation assembly is in the proximal position, wherein the deflectable distal portion of the second shaft is configured to be positioned about the malleable distal portion of the first shaft when the actuation assembly is in the distal position.

5. The apparatus of claim 1, wherein the actuator is positioned at a proximal end of the second shaft.

6. The apparatus of claim 5, wherein the actuator is positioned distal to the body.

7. The apparatus of claim 1, wherein the actuation assembly is operable to translate relative to the body along the first shaft.

8. The apparatus of claim 1, wherein the actuator comprises a first member and a second member, wherein the first member is rotatable relative to the second member to selectively bend the malleable distal portion of the first shaft.

9. The apparatus of claim 8, wherein the first member comprises a rotary knob rotatable relative to the second shaft, wherein the second member comprises a stationary knob fixedly secured relative to the second shaft.

10. The apparatus of claim 8, wherein the actuator further comprises a translating member, wherein the translating member is configured to translate and thereby selectively bend the malleable distal portion of the first shaft in response to rotation of the first member relative to the second member.

11. The apparatus of claim 10, wherein the translating member comprises a wire.

12. The apparatus of claim 1, wherein first shaft and the actuation assembly include features configured to prevent rotation of the second shaft relative to the first shaft.

13. The apparatus of claim 1, further comprising a slider slidably coupled with the body, wherein the slider is operable to drive the dilation catheter longitudinally along the first shaft.

14. The apparatus of claim 1, wherein the dilator in a non-expanded state is configured to fit in an anatomical passageway in a human head, wherein the dilator in an expanded state is configured to dilate the anatomical passageway.

15. The apparatus of claim 1, wherein the dilation catheter is operable to translate between a proximal position and a distal position, wherein the dilator is configured to be positioned distal to a distal end of the first shaft when the dilation catheter is in the distal position.

16. The apparatus of claim 15, wherein the dilator is configured to be positioned proximal to a distal end of the second shaft when the dilation catheter is in the proximal position.

17. An apparatus, comprising:
(a) a body;
(b) a shaft assembly extending distally relative to the body, wherein the shaft assembly comprises:
   (i) a first shaft, wherein the first shaft includes a malleable distal portion, and
   (ii) a second shaft, wherein the second shaft is coaxially positioned about the first shaft, wherein the second shaft includes a deflectable portion;
(c) an actuator, wherein the actuator is operable to selectively drive the deflectable portion to bend the malleable distal portion of the first shaft; and
(d) a dilation catheter coaxially interposed between the first shaft and the second shaft, wherein the dilation catheter includes an expandable dilator, wherein the dilation catheter is operable to translate along the malleable distal portion of the first shaft.

18. The apparatus of claim 17, wherein the actuator is secured to a proximal portion of the second shaft.

* * * * *